(12) United States Patent
Bucknall et al.

(10) Patent No.: US 9,375,512 B2
(45) Date of Patent: Jun. 28, 2016

(54) TISSUE EXPANDER

(75) Inventors: David Bucknall, Summertown (GB); Jan Czernuszk, Summertown (GB); Jinhyun Lee, Summertown (GB); Zamri Radzi, Summertown (GB); Marc Swan, Summertown (GB)

(73) Assignee: ISIS INNOVATION LTD., Summertown, Oxfordshire (GB)

( * ) Notice: Subject to any disclaimer, the term of this patent is extended or adjusted under 35 U.S.C. 154(b) by 191 days.

(21) Appl. No.: 13/499,972

(22) PCT Filed: Nov. 1, 2010

(86) PCT No.: PCT/GB2010/051828
§ 371 (c)(1),
(2), (4) Date: Jun. 25, 2012

(87) PCT Pub. No.: WO2011/051731
PCT Pub. Date: May 5, 2011

(65) Prior Publication Data
US 2012/0265165 A1    Oct. 18, 2012

Related U.S. Application Data (60) Provisional application No. 61/256,637, filed on Oct. 30, 2009.

(30) Foreign Application Priority Data

Feb. 22, 2010 (GB) .................................. 1002959.3

(51) Int. Cl.
| | | |
|---|---|---|
| A61L 27/26 | (2006.01) |
| A61L 27/50 | (2006.01) |
| A61L 27/52 | (2006.01) |
| A61L 27/58 | (2006.01) |
| A61L 31/04 | (2006.01) |
| A61L 31/14 | (2006.01) |
| A61B 19/00 | (2006.01) |

(52) U.S. Cl.
CPC .................. *A61L 27/26* (2013.01); *A61B 19/24* (2013.01); *A61L 27/50* (2013.01); *A61L 27/52* (2013.01); *A61L 27/58* (2013.01); *A61L 31/04* (2013.01); *A61L 31/14* (2013.01); *A61L 31/148* (2013.01)

(58) Field of Classification Search
USPC ....................................................... 521/134
See application file for complete search history.

(56) References Cited

U.S. PATENT DOCUMENTS

| | | | |
|---|---|---|---|
| 5,005,591 A * | 4/1991 | Austad ......................... | 128/899 |
| 2003/0055506 A1 | 3/2003 | Stoy et al. | |
| 2007/0031499 A1 | 2/2007 | Huh et al. | |

FOREIGN PATENT DOCUMENTS

WO    2007080391 A2    7/2007

* cited by examiner

*Primary Examiner* — Samuel Woolwine
*Assistant Examiner* — Valerie Toodle
(74) *Attorney, Agent, or Firm* — Rothwell, Figg, Ernst & Manbeck, P.C.

(57) ABSTRACT

This invention relates to a tissue expander for use in medical, veterinary and dental applications. The tissue expander comprises a self-inflating polymer network and a biodegradable polymer having a non-degraded state and a degraded state which in the non-degraded state constrains the inflation of the self-inflating polymer network and in the degraded state allows inflation of the self-inflating polymer network. In a preferred embodiment, the self-inflating polymer network and the biodegradable polymer form an interpenetrating polymer network or a semi-interpenetrating polymer network. Alternatively or in addition, the self-inflating polymer network forms a core and the biodegradable polymer forms coating which partially or fully surrounds the core.

14 Claims, 6 Drawing Sheets

TISSUE EXPANDER

This application is a filing under 35 USC 371 of PCT/GB2010/051828, filed 1 Nov. 2010, which claims priority from U.S. Application 61/256,637, filed 30 Oct. 2009 and GB Application 1002959.3, filed 22 Feb. 2010. These prior applications are incorporated herein by reference.

This invention relates to a tissue expander and particularly to a tissue expander for use in medical, veterinary and dental applications.

Tissue expansion has evolved from a surgical curiosity to become a valuable and firmly established technique in reconstructive plastic surgery, for example in treating congenital abnormalities and acquired tissue defects.

Conventional tissue expanders are based on a silicone balloon which is introduced into the required area and then sequentially inflated via a filling port with saline solution over a period of time. These tissue expanders may also be designed to allow anisotropic expansion, see for example U.S. Pat. No. 6,228,116. However, the application of these balloon-type tissue expanders has been limited. This is in part related to the physical constraints of the device, which often preclude their use in some anatomical locations (e.g. craniofacial or cleft palate surgery), but also due to the requirement for regular percutaneous inflation, which can be poorly tolerated by the patient, particularly in the paediatric setting.

To address these problems, self-inflating tissue expanders have been proposed, i.e. tissue expanders which inflate without requiring any intervention once implanted. Initially, these expanders were relatively crude, being based on a semipermeable membrane shell containing hypertonic sodium chloride solution. Once implanted into the patient, osmotically driven swelling of the device occurs with concomitant tissue expansion. However, limitations existed both in the rate and extent of expansion and the inherent risk of catastrophic soft tissue necrosis in the event of device rupture.

To address this problem, hydrogels (a gel in which water is the dispersion medium) have been investigated for use in tissue expanders. For example, U.S. Pat. No. 5,496,368 discloses an osmotically active polymer-based tissue expander which was proposed for the treatment of congenital anophthalmia. Additionally, WO 2007/080391 discloses a self-inflating anisotropic device based on a compressed co-polymer which is preferably in the form of a hydrogel.

However, research work carried out by the present inventors has shown that the rapid swelling of these hydrogel-based devices may result in localised tissue necrosis which can compromise healing of the surgical incision and possibly result in device extrusion. There is therefore a requirement in the art for devices with a more controlled swelling rate.

Accordingly, the present invention provides a tissue expander comprising a self-inflating polymer network and a biodegradable polymer having a non-degraded state and a degraded state which in the non-degraded state constrains the inflation of the self-inflating polymer network and in the degraded state allows inflation of the self-inflating polymer network.

Thus, the tissue expander contains a polymer network which is only prevented from expanding by a biodegradable polymer which in turn degrades in vivo in a controlled manner to allow controlled expansion of the polymer network. This provides considerable benefit to the patient, in particular allowing time for wound healing before tissue expansion and/or slower expansion once expansion has begun.

The present invention will now be described with reference to the accompanying drawings, in which.

A tissue expander thus comprises a self-inflating polymer network and a biodegradable polymer which constrains the inflation of the self-inflating polymer network in a controlled manner. The self-inflating polymer network of the present invention is based on a hydrophilic polymer network which is capable of absorbing water without dissolution. The hydrophilic properties are provided by functional groups on the polymer(s) (e.g. hydroxyl, carboxyl or amide functional groups). Preferably the self-inflating polymer network comprises at least one monomer containing —COOH, >C=O, —OH, or —NH$_2$ groups. The resistance to dissolution is a result of the presence of structural cross-linkages, crystalline regions or entanglements. Such materials are typically termed "hydrogels". The hydrogel contains two components, namely the polymer network (i.e. the gel), which is constant in quantity, and a variable aqueous component. In the anhydrous state (prior to implantation), the material is normally referred to as a xerogel. The anhydrous material is hygroscopic and absorbs/adsorbs water from its local environment to hydrate the network. The self-inflating polymer network may swell to many times its dry mass. Typically, the aqueous phase comprises 90% or more, preferably 95% or more of the total mass of the self-inflating polymer network at equilibrium.

The expansion of the self-inflating polymer network is driven by the diffusion of water molecules into the polymer network which is due to osmosis and the interaction between the polymer and water molecules in order to reduce the Gibbs free energy of the system when the polymer is introduced into an aqueous environment, i.e. from tissue fluid in vivo. The self-inflating polymer network approaches its equilibrium state when the driving force for the mixing between the polymer species and the solvent is balanced by the restoring force of the chains in the network due to the elasticity of polymer network.

Compression may be introduced by applying heat and pressure to the isotropic polymer network. This is typically applied in one direction or plane to provide a subsequent anisotropic expansion principally in the direction of compression. The combination of heat at around or above the glass transition temperature ($T_g$) of the polymer and pressure causes the molecular chains to realign. Clearly heating should be lower than the degradation temperature of the polymer. The swelling pressure is provided by the hydration of the polymer network (e.g. xerogel) to form a fully swollen polymer network (e.g. a hydrogel) which occurs in vivo. The self-inflating polymer network is preferably a xerogel/hydrogel, i.e. the network changes from a xerogel to a hydrogel as it absorbs water in vivo. The self-inflating polymer network preferably generates a swelling pressure of 1-50 kPa/cm², and more preferably 2-20 kPa/cm². The absolute swelling pressure may be up to 100 kPa.

Figure 1:
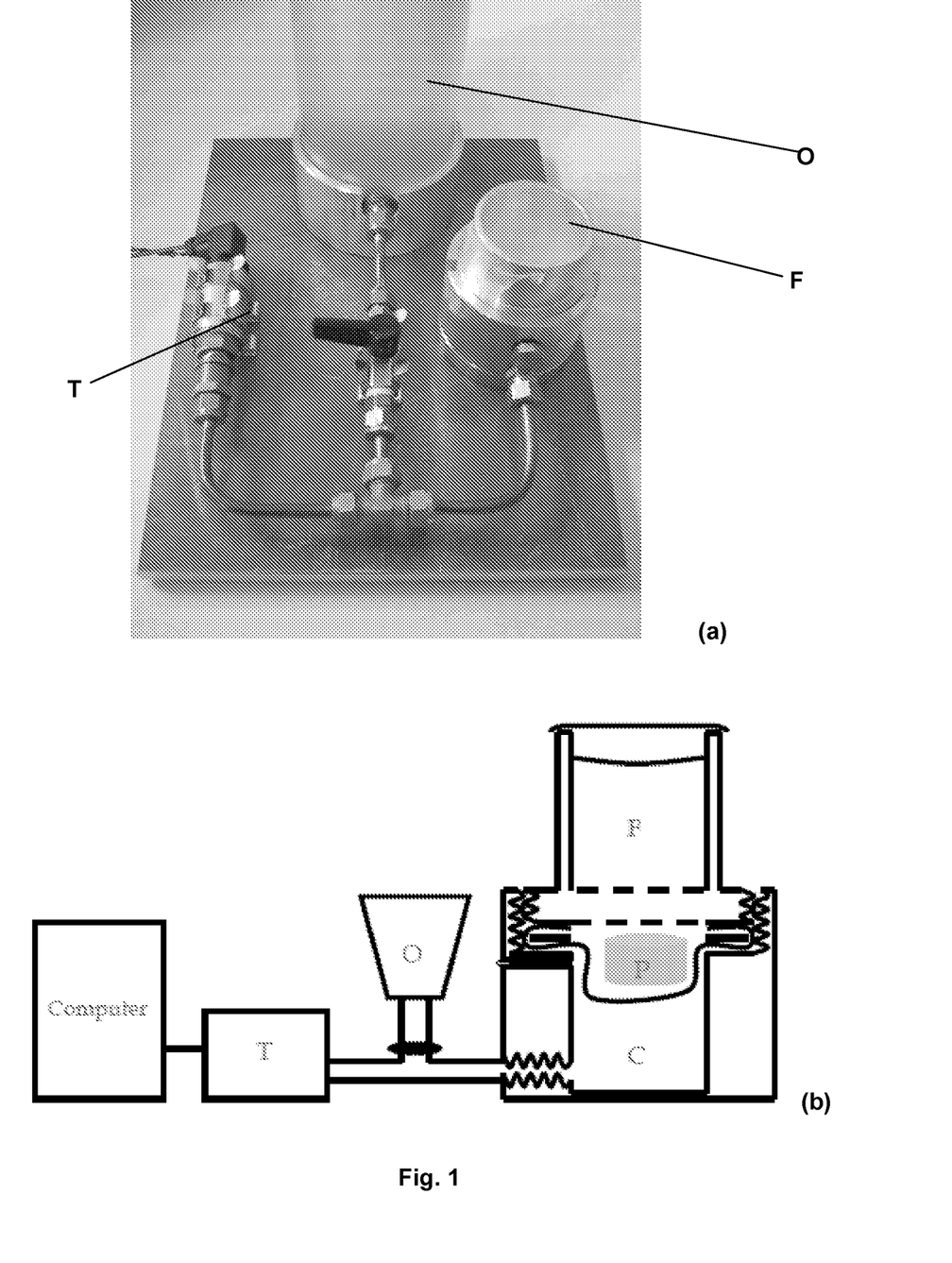
FIG. 1 shows the apparatus used for measuring the swelling pressure of the polymer network of the present invention.

The in vitro swelling pressure of the self-inflating polymer may be measured using an instrument (see FIG. 1) following the design described by K. G. Wiese, Osmotically induced tissue expansion with hydrogels: a new dimension in tissue expansion? A preliminary report. Journal of Craniomaxillofacial Surgery 1993; 21 (7): 309-313. FIG. 1(a) shows a photograph of the apparatus and FIG. 1(b) shows a schematic representation. The apparatus comprises an oil reservoir O, a fluid reservoir F, a polymer P within an expansion chamber, a compression chamber C and a pressure transducer T. The anisotropic xerogel cylinder (compression ratio=3, see below) is sealed within the aluminium expansion chamber, which is separated from the oil filled compression chamber by means of a latex diaphragm. Hartmann's solution from the fluid reservoir was then allowed to fill the expansion chamber via the separating perforated plate. As the hydrogel absorbs fluid from the reservoir, resultant swelling deflects the latex diaphragm thus compressing the oil contained within the compression chamber. The increase in pressure within the compression chamber is detected by a pressure transducer, from which the electrical output can be recorded by commercially available data acquisition software.

The expansion of the tissue expander may be uniform (isotropic expansion) or may be in a given direction or plane (anisotropic expansion). The compression ratio can be altered to manipulate the specific characteristics of the tissue expander. The compression ratio is the ratio of the thickness of the uncompressed polymer network to the compressed network. For example, if an amount of co-polymer is compressed to a third of the original amount, the compression ratio is 3:1. The compression ratio alters the final degree of overall expansion. The greater the compression ratio, the greater the overall expansion. Preferable ratios may include from 2:1, 3:1, 4:1 or 5:1 through to 20:1 and more preferably through to 15:1. The preferable compression strain rate is in the order $10^{-5}$ to $10^{-1}$ per second. The compression modulus of the hydrated polymer network is preferably 0.01-0.5 MPa, preferably 0.03-0.2 MPa.

Hydrogels are broadly classified into two structural forms. The structurally stable gels are covalently cross-linked networks and are termed "permanent" or "chemical" gels, whereas those prone to degradation are termed "reversible" or "physical" gels and are bound by either molecular entanglements or non-covalent bonding such as ionic interactions, van der Waals interactions or hydrogen bonds. The equilibrium swelling state of cross-linked hydrogels is in part governed by the cross-linking density of the polymer, which can be estimated by the molecular weight between cross-links ($M_c$). Both chemical and physical gels exhibit structural inhomogeneity due to variable clusters of hydrophilic domains or high cross-linking density. Permanent hydrogels can be synthesised by in situ monomer polymerisation in the presence of one or more bifunctional monomers, or by cross-linking preformed polymers or co-polymers, using a method such as thermal polymerisation, gamma irradiation or photo-polymerisation.

The polymer may be formed by standard polymerisation techniques well known in the art. For example, the polymerisation technique can include chain-growth polymerisation. The method involves three stages comprising initiation, propagation and termination (see, for example, Chapter 1 and 3, of George Ordian, Principles of Polymerization $4^{th}$ Ed, Wiley-Interscience, 2004). A co-polymer may be produced by co-polymerising two or more monomers together. An initiator may be used to initiate the polymerisation reaction and the polymer cross-linked using a cross-linker.

The resulting polymer typically has a weight average molecular weight between cross-links (Mc) within the range of 1,000 to 500,000 g/mol.

The polymers may be thermoplastic or thermoset, but are preferably thermoplastic. They may be either amorphous or semi-crystalline in structure. The polymers may also be non-ionic, ionic or ampholytic. Ionic polymers provide an increase in the osmotic potential of the polymer network and thus augment the degree of swelling which can be beneficial in some applications. Methacrylic acid is an example of an agent which may be used during the polymerisation process partially to ionise the polymer.

The polymer network may be a co-polymer with at least one hydrophilic component. The co-polymer may be a random, alternating, block or graft co-polymer. The proportion of the first and second or further monomers in the co-polymer or blend may be varied depending on the required specification of the tissue expander which will, in turn, depend on the clinical application.

The self-inflating polymer network of the present invention may also be based on the compressed co-polymer set out in WO 2007/080391, in which case this network contains a first component which is hygroscopic and a second component which provides a scaffold (backbone) to the network. The second component may also have hygroscopic properties.

The first component preferably contains —COOH, >C=O, —OH, or —NH₂ groups, such as vinylpyrrolidone, acrylamide, vinyl alcohol, N-cyclopropylacrylamide, N-n-propylacrylamide, N-isopropylacrylamide, acrylic acid, ethylene oxide or methacrylic acid.

The second component may be based on the first component described hereinabove or, preferably, an acrylate. In particular, the second component may be selected from the following monomers: methyl methacrylate, glyceryl methacrylate, hydroxyethyl methacrylate, ethyl methacrylate, i-butyl methacrylate, t-butyl methacrylate, n-hexyl methacrylate, 2-ethylhexyl methacrylate, isodecyl methacrylate, dodecyl methacrylate, methacrylic ester, octadecyl methacrylate, cyclohexyl methacrylate, isobornyl methacrylate, benzyl methacrylate, trimethylcyclohexyl methacrylate, isotridecyl methacrylate, methacrylic acid, acrylic acid, methacrylic anhydride, maleic acid, isobornyl acrylate, urethane, and (ethylene-co-vinyl acetate).

A preferred polymer is a diblock co-polymer of N-vinyl-2-pyrrolidone (NVP) and either hydroxyethylmethacrylate (HEMA) or methyl methacrylate (MMA). Poly(HEMA-co-NVP) or poly(MMA-co-NVP) co-polymers are formed by co-polymerisation of NVP with HEMA or MMA in the presence of a cross-linking agent (e.g. ethylene dimethacrylate, EDMA) in order to produce hydrogels which have the advantage of remaining insoluble once hydrated. Increasing the proportion of NVP within the co-polymer results in an increased swelling ratio. Poly(MMA-co-NVP) co-polymers have been shown to produce an in vitro swelling pressure in isotonic saline of approximately 31.3 kPa (235 mmHg) and additional expansion could be achieved by ionising the gel during processing. Methacrylic acid can be used to convert methyl moieties into carboxyl groups, which on hydration are able to dissociate into carboxylate anions and hydrogen ions thus increasing the osmotic potential of the polymer and thus the swelling ratio. See K. G. Wiese, Osmotically induced tissue expansion with hydrogels: a new dimension in tissue expansion? A preliminary report. Journal of Craniomaxillofacial Surgery 1993; 21 (7): 309-313 for further details.

Other suitable cross-linking agents include N,N'-methylenebisacrylamide (BIS), ethylene glycol dimethacrylate (EGDMA), diethylene glycol diacrylate (DEGDA), diethylene diacrylate (DEDA), allyl methacrylate or 1,4-butanedioldiacrylate. The cross-linker is preferably used at 0.005 to 1.0 wt % based on the total weight of the components of this reaction. The reaction may use an initiator selected from 2,2'-azobisisobutyronitrile (AIBN), benzoyl peroxide (BPO), ammonium persulfate/tetramethylethylenediamine (APS/TMEDA) or potassium persulfate (KPS)/TMEDA. The initiator is preferably used at 0.01 to 1.0 wt % based on the total weight of the components of this reaction.

The Young's modulus of the hydrogel increases as a function of the concentration of cross-linker used.

The self-inflating polymer network preferably comprises at least two monomers, which preferably constitutes a co-polymer as described hereinabove or a two different homopolymers which are cross-linked, but may also be a polymer blend employing the first and second polymers described hereinabove which form a network without covalent cross-linking. Each component generally retains its innate chemical and physical properties, and overall, the functionality of is controlled by altering the relative concentrations of the components. Preferably the polymer network contains at least two types of monomers and hence is preferably a co-polymer or a blend of two polymers. The proportion of the first and second or further monomers in the co-polymer or blend may be varied depending on the required specification of the tissue expander which will, in turn, depend on the clinical application.

Alternatively, the polymer network may be based on a homopolymer. Suitable materials include poly(hydroxyalkyl methacrylate), such as poly(2-hydroxyethyl methacrylate) (PHEMA) or poly(glyceryl methacrylate) (PGMA). The carbonyl group and the terminal hydroxyl group render the monomer hydrophilic, whereas the α-methyl group and backbone impart a degree of hydrophobicity and hydrolytic stability. Accordingly, these polymers may be used as the sole polymer of the self-expanding network. However, a constraint of some poly(hydroxyalkyl methacrylate) hydrogels is their limited swelling and poor mechanical strength in the xerogel state.

The tissue expander of the present invention also contains a biodegradable polymer. Biodegradable polymers are known in the art. Such polymers are initially in a non-degraded state. Once introduced in vivo, covalent bonds in the biodegradable polymer are broken and the polymer degrades into smaller fragments. The degradation is typically by hydrolysis or by enzymatic degradation or a combination thereof. Over time, the biodegradable polymer is reduced to a degraded state.

Prior to implantation, the biodegradable polymer is in a non-degraded state and in this state restricts the inflation of the self-inflating polymer network by physical means. This may be, for example, by forming an interpenetrating polymer network or by coating the self-inflating polymer, as discussed in further detail hereinbelow. After the implantation, the biodegradable polymeric chains start to degrade after a certain time period depending on the nature of the biodegradable polymer. As the biodegradable polymer degrades, the degraded fragments become less and less able to constrain the self-inflating polymer network. As the biodegradable polymers fully degrade, the equilibrium degree of swelling of the self-expanding polymer network can be the final equilibrium degree of swelling of the tissue expander.

The time and rate at which the biodegradable polymer degrades will depend on the nature of the polymer used, the expansion pressure provided by the self-inflating polymer network, and the local environmental conditions of the implant and the nature of the patient. Different clinical applications will also require different rates of expansion. The polymer may also be designed to delay the expansion of the self-inflating polymer network and/or reduce the rate of expansion once expansion begins. In a preferred embodiment, the biodegradable polymer degrades from the non-degraded state to the degraded state over a period of 12 hours to six months, more preferably over at least 2 days, more preferably over at least 7 days and most preferably over 2 to 12 weeks. This is primarily to allow wound healing prior to expansion and to control the subsequent expansion rate. In contrast, current expanders swell as early as 24-48 hours after implantation in an uncontrolled manner.

The biodegradable polymer is preferably based on a macromer selected from polymers or co-polymers of glycolic acid and/or lactic acid (e.g. polylactic acid (PLA), polyglycolic acid (PGA), poly(lactic-co-glycolic acid) (PLGA), poly (glycolide-co-trimethylene carbonate) (PGA-TMC), or poly (lactide-co-ε-caprolactone) (PLCL)), poly(dioxanone) (PDO), poly(trimethylene carbonate) (PTMC), poly(ε-caprolactone) (PCL), polyanhydrides (e.g. poly(sebacic acid-co-hexadecandioic acid anhydride) (poly(SA-co-HA)), polyhydroxybutyrate (PHV), polyorthoesters, polyketals (e.g. poly (phenyleneacetone dimethylene ketal) (PPADK), poly (cyclohexane-1,4-diyl acetone dimethylene ketal) (PCADK)), polyacetals, polyphosphazenes, polyhydroxybutyrate (PHB), polyhydroxyvalerate (PHV), polycyanoacrylates, poly(amino acids), poly(propylene fumarate), fibrin, collagen, gelatin, hyaluronan, chondrin, starch, glycogen, cellulose and chitosan, as well as polymer blends and co-polymers of two or more of these polymers.

The macromer forming the biodegradable polymer may be cross-linked using one or more of the following cross-linkers: N,N'-methylenebisacrylamide (BIS), ethylene glycol dimethacrylate (EGDMA), diethylene glycol diacrylate (DEGDA), diethylene diacrylate (DEDA), allyl methacrylate or 1,4-butanedioldiacrylate. The cross-linker is preferably used at 0.005 to 1.0 wt % based on the amount of macromer, cross-linker and initiator. The reaction may use an initiator selected from 2,2'-azobisisobutyronitrile (AIBN), benzoyl peroxide (BPO), ammonium persulfate/tetramethylethylenediamine (APS/TMEDA) or potassium persulfate (KPS)/TEMDA. The initiator is preferably used at 0.01 to 1.0 wt % based on the amount of macromer, cross-linker and initiator.

The resulting biodegradable polymer has a weight average molecular weight typically between cross-links ($M_c$) within the range of 1,000 to 500,000 g/mol. The biodegradable polymer preferably has a glass transition temperature which is similar to the glass transition temperature of the self-inflating polymer network. The molecular weight and nature of the polymer, for example derivatives of the above polymers, is chosen to achieve the desired glass transition temperature. By "similar" is meant a glass transition temperature of the biodegradable polymer within ±20° C. of the self-inflating polymer network.

The biodegradable polymer physically constrains the inflation of the self-inflating polymer network when it is in a non-degraded state, i.e. prior to implantation and hence needs to have a sufficient strength to restrict the expansion. Preferably the biodegradable polymer has a modulus of 0.01 to 10 GPa (in its xerogel state). The modulus may be measured by techniques known in the art, such as using a dynamic mechanical analyser (DMA). The measurement is performed on the biodegradable polymer in the absence of the self-inflating polymer.

In a preferred embodiment, the biodegradable polymer constrains the self-inflating polymer network forming an interpenetrating polymer network (IPN). Accordingly, in a preferred embodiment of the present invention, the self-inflating polymer network and the biodegradable polymer form an IPN. In the IPN, the self-inflating polymer network may be termed the primary network and the biodegradable polymer may be termed the secondary network.

An IPN may be defined as a polymer comprising two or more networks which are at least partially interlaced on a molecular scale but are not covalently bonded to one another and cannot be separated without breaking covalent bonds (see the IUPAC Compendium of Chemical Terminology, 2nd Edition 1997). The interpenetration of the self-inflating polymer network and the biodegradable polymer prevents the self-inflating polymer network from expanding by mechanical interlocking. Since an IPN cannot be disrupted without breaking covalent bonds, the tissue expander may be maintained in this non-expanded state for some time. However, degradation of the biodegradable polymer leads to the disruption of the IPN allowing expansion of the self-inflating polymer network.

In another embodiment, the biodegradable polymer constrains the self-inflating polymer network forming a semi-interpenetrating polymer network (SIPN). In this case, the self-inflating polymer network and the biodegradable polymer form a SIPN.

A SIPN is a polymer comprising a network and a linear or branched polymer characterised by a penetration on a molecular scale of the network by the linear or branched polymer (see the IUPAC Compendium of Chemical Terminology, 2nd Edition 1997). SIPNs are distinguished from IPNs because the constituent linear or branched polymers can, in principle, be separated from the constituent polymer network without breaking chemical bonds.

Figure 2:
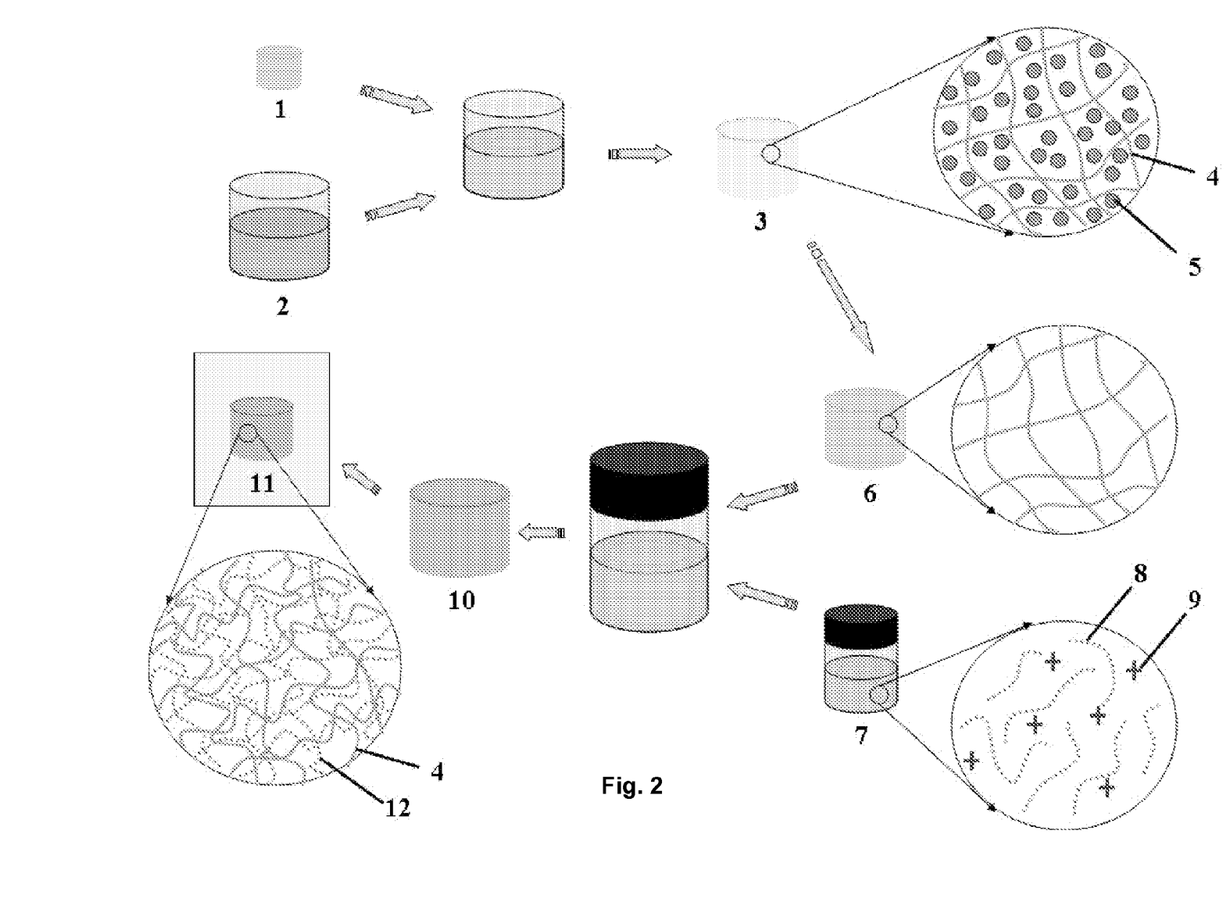
FIG. 2 shows a schematic representation of an interpenetrating polymer network suitable for use as a tissue expander in accordance with the present invention.

A schematic representation of the preparation of an IPN of a hydrogel and a biodegradable polymer is shown in FIG. 2. A xerogel 1, such as poly(MMA-co-NVP), is introduced into a swelling medium 2, such as water. The xerogel becomes hydrated to form a fully swollen hydrogel 3. The hydrogel 3 is composed of a polymer network 4 and water molecules 5. The water 4 is then removed from the hydrogel 3, for example by desiccation or freeze drying to form a xerogel 6. Drying in this manner maintains the network structure 4 but removes the water. The fully swollen hydrogel 3 is typically freeze-dried for 3-4 days. Removal of the solvent (e.g. water) allows the components of the biocompatible polymer (i.e. macromers in solution with cross-linkers) to penetrate effectively. The macromer solution 7 comprising the component parts of the biodegradable polymer is then prepared. The macromer solution 7 comprises the biodegradable macromer 8 and a cross-linker 9, together with a solvent. The biodegradable macromer is functionalised by end-capping with unsaturated groups. The degree of end-capping may be determined by X-ray photoelectron spectroscopy (XPS), infrared (IR) spectroscopy and/or nuclear magnetic resonance spectroscopy (NMR). The freeze dried gel 7 is combined with the macromer solution and the components are allowed to diffuse into the gel network. An initiator is then added to initiate the reaction of the macromer and cross-linker to form the biodegradable network. The mixture is allowed to react at appropriate temperature, pressure and time, for example for 6-12 h at 60-70° C. and 67 KPa (500 mmHg) to form a wet IPN gel 10. The wet IPN gel 10 is then purified and dried to provide the dry IPN 11 composed of an IPN of the self-expanding polymer 4 and the biodegradable polymer network 12. The obtained IPN may be characterised by Differential Scanning calorimetry (DSC), Thermogravimetric Analysis (TGA), Fourier Transform Infrared (FTIR) spectroscopy, Scanning Electron Microscopy (SEM), mechanical tests, biocompatible assays and swelling measurements. When a biodegradable polymer solution is used instead of the macromer solution and the reaction by initiator is not preceded, SIPN gels are obtained. The biodegradable polymers instead of the biodegradable network will interpenetrate the primary network in the SIPN structure.

Figure 3:
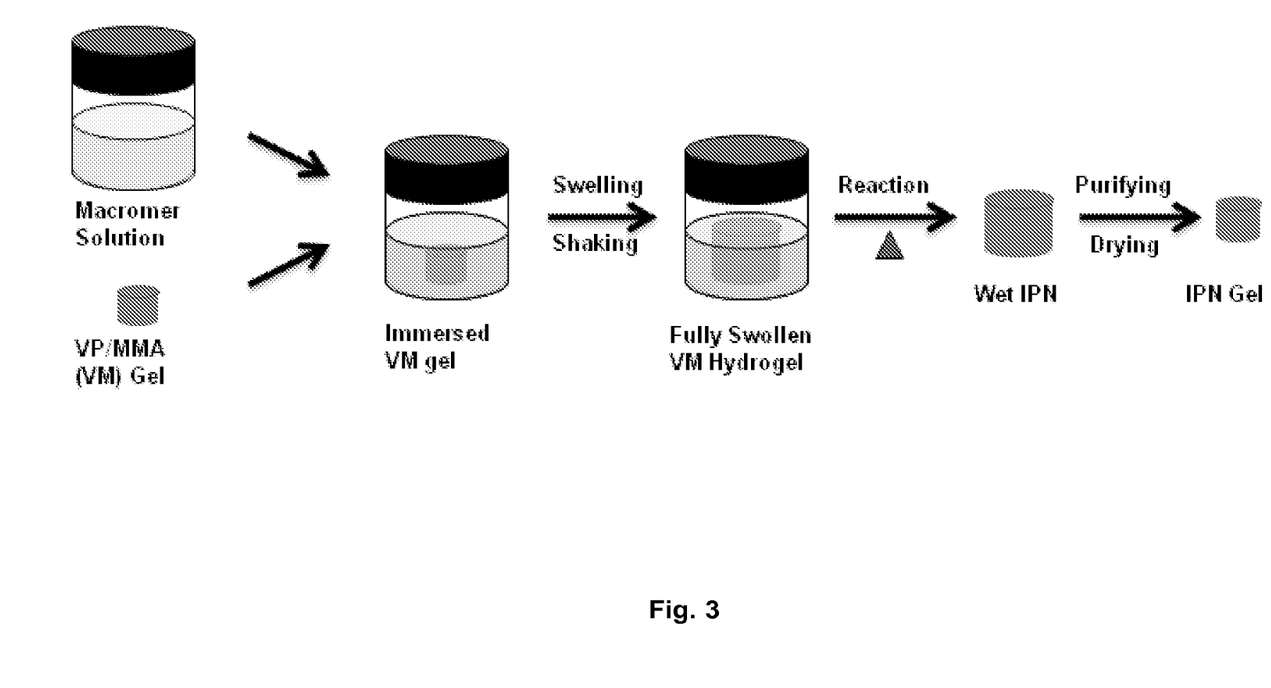
FIG. 3 shows a further schematic representation of an interpenetrating polymer network suitable for use as a tissue expander in accordance with the present invention.

Alternatively, as shown in FIG. 3, a xerogel, such as poly(MMA-co-NVP), can be introduced into a macromer solution, e.g. PLGA, and become a fully swollen hydrogel. An initiator, e.g. N,N'-methylenebisacrylamide (BIS), is then added to initiate the reaction for forming the IPN gel. When a biodegradable polymer solution is used instead of the macromer solution and the reaction by initiator is not preceded, SIPN gels are obtained. The biodegradable polymers instead of the biodegradable network will interpenetrate the primary network in the SIPN structure. The immersion time of a xerogel in the macromer solution may also be modulated to influence the content and morphological structure of the IPN gel to be formed.

The dry IPN (or SIPN) material may be compressed if anisotropic swelling is required. The compression is performed by heating the material at or close to (e.g. within 20° C., preferably 5° C.) or above its glass transition temperature, compressing the composition, and then allowing the composition to cool. The compression step may be in one direction. The compression may be carried out using any compression technique known in the art, such as a hand or machine operated hydraulic press with thermostatically controlled heated plates which are commercially available, e.g. from Specac Ltd, Orpington, Kent. The pressure required depends on the level of compression to be achieved, but is typically in the region of 1 kPa to 500 MPa. Preferably, the material is heated to approximately the glass transition temperature of the co-polymer for at least 30 minutes. The temperature will, of course, depend on the nature of the polymers, but is usually around 35-250° C. It is preferable to maintain the temperature during compression to approximately the glass transition temperature of the material. The material is then allowed to cool to below the glass transition temperature, preferably while maintaining the compression. The resulting compressed xerogel is then removed from the holding or constraining device. This allows subsequent expansion when in use.

Finally, the swelling behaviour and degradation rate of the IPN (or SIPN) hydrogels may be investigated.

Figure 4:
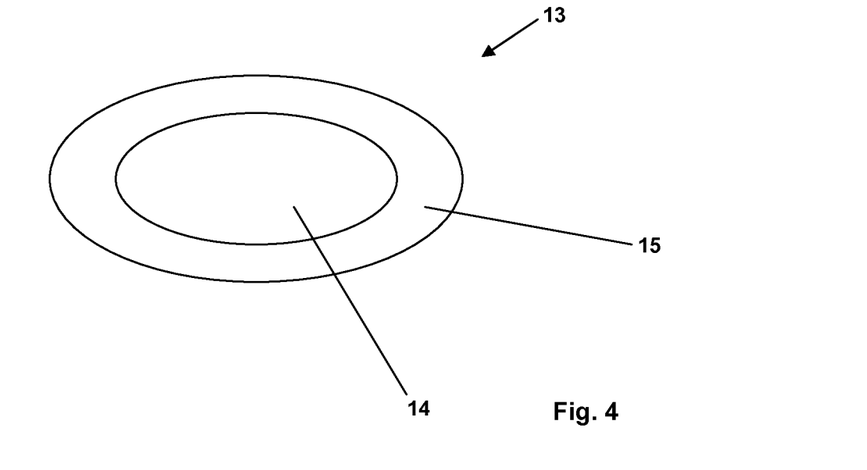
FIG. 4 shows a self-inflating polymer network coated with a biodegradable polymer in accordance with the present invention.

FIG. 4 shows a further embodiment of the tissue expander 13 of the present invention. The self-inflating polymer network forms a core 14 and the biodegradable polymer forms coating 15 which surrounds the core. The biodegradable polymer may surround the core partially or fully. By surrounding the core in this manner, the expansion of the self-inflating polymer network may also be constrained. The coating of core may be used as the sole constraint, or the core may also comprise an IPN of the self-inflating polymer network and the biodegradable polymer as described hereinabove. Combining the two approaches provides further control over the time delay prior to expansion and the rate of expansion once degradation of the biodegradable polymer has commenced.

The compression may be achieved either before or after introducing the biodegradable polymer layer.

Figure 5:
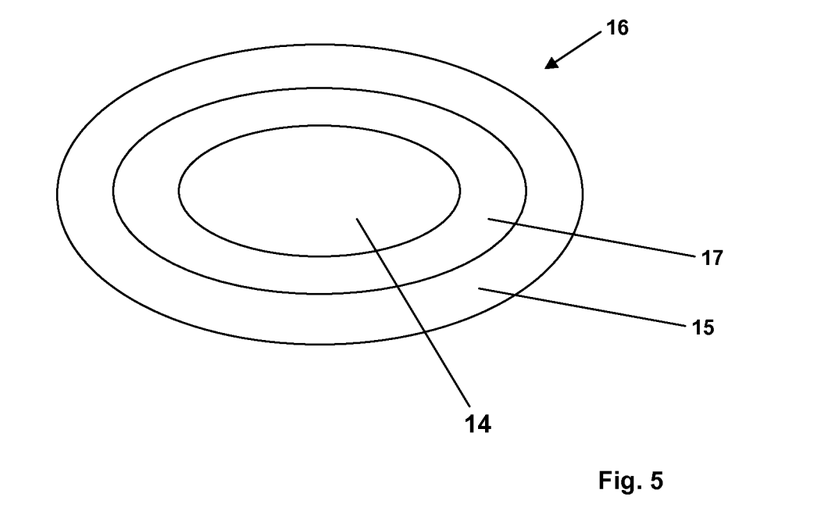
FIG. 5 shows a self-inflating polymer network coated with a biodegradable polymer in accordance with the present invention, together with an additional silicone layer.

As shown in FIG. 5, the tissue expander 6 may further comprise a coating layer 17 (or an additional coating layer) and the nature of the coating layer 17 may be manipulated to alter the rate of diffusion into the tissue expander. In particular, the following factors affect the rate of diffusion: the thickness of the coating; the elasticity and the mechanical strength of the coating; and the permeability.

The coating may be composed of an inert material, such as silicone, polyvinyl alcohol, cellulose acetate, polybutadiene or combinations thereof. The coating layer can be perforated or semi-permeable. The presence and number of perforations can be manipulated to alter the rate of diffusion into the tissue expander.

There is an inverse relationship between the thickness of the silicone coating and the swelling ratio of the expander, i.e. the thicker the coating, the slower the diffusion rate, thus the swelling rate is also reduced. The thickness of the coating layer is preferably 250 microns or less. Thinning of the silicone coating will increase the diffusion and swelling rate; however, the coating must not be so thin as to compromise the mechanical strength of the coating.

In a preferred embodiment, the coating layer 17 contains water-soluble filler particles. The filler particles are dispersed in the coating layer and help to control the permeability of the coating layer. The presence of the filler particles allows the coating layer to be thicker whilst retaining permeability. By "water soluble" is meant that the filler particles are soluble in water at 25° C. and "soluble" takes the definition given in the British Pharmacopeia, namely that 1 g of solute dissolves in 30 mL or less of solvent. The solubility is determined for the filler as a whole and hence hybrid fillers may be used with each component providing a different contribution to the overall solubility of the filler. Suitable examples include salts and saccharides, for example sodium chloride (solubility of in water: 36 g/100 g of water at 25° C.), potassium chloride (solubility of in water: 36 g/100 g of water at 25° C.), glucose (solubility of in water: 100 g/100 g of water at 25° C.), maltose (soluble in water), or combinations thereof.

The particles preferably have a sieved particle size of 100 microns or less, more preferably 40 microns or less, and most preferably 20 microns or less. The minimum size is less important, but will typically be 1 micron or above. The volume fraction of the water-soluble filler particles is preferably 0.1-20%, more preferably 0.1-5%. In a particularly preferred embodiment the, the coating layer includes 5 volume percent of 20 micron or less sodium chloride which reduces the swelling ratio from 7.4 to 5.8 without significantly affecting the final size of the tissue expander.

The coating may also contain a radio-opacifier to allow for X-ray detection (e.g. barium sulfate or silver, which is both radio-opaque and anti-microbial).

The present invention also provides a process for preparing a tissue expander comprising the steps of (i) providing a self-inflating polymer network, (ii) optionally compressing the polymer network (iii) applying a biodegradable polymer having a non-degraded state and a degraded state which in the non-degraded state constrains the inflation of the self-inflating polymer network and in the degraded state allows inflation of the self-inflating polymer network, wherein steps (ii) and (iii) may be performed in either order. Preferably, the process is for preparing an IPN, SIPN or a coated structure as described hereinabove. When step (ii) is included, in the case of an IPN or SIPN, step (iii) preferably precedes step (ii) whereas for the coated structure, step (ii) preferably precedes step (iii).

As the tissue expander is used as a surgical implant, it is beneficial that the composition is sterile. Sterilisation may be by gamma irradiation or by another method of sterilisation that does not cause the tissue expander to absorb water and expand prematurely, such as electron beam sterilisation, treatment with ethylene oxide or use of a steam autoclave. The tissue expander is surgically implantable in the human or animal body, preferably under local, regional or general anaesthetic. The tissue expander may also include additional components, such as pharmaceutically active ingredients (i.e. drugs), e.g. antibiotics, analgesics or anti-inflammatory agents, and/or radio-opacifiers.

The tissue expander is biocompatible and has a smooth surface in order to minimise the risk of extrusion. It typically has a size from 1 mm to 30 cm to suit a wide range of surgical applications.

The tissue expander can be machined or shaped into any desired configuration and thus anatomically tailored for any application. The tissue expander may also be shaped by the surgeon during implantation, particularly where the tissue expander does not have a coating. This is a particular advantage of the tissue expander in the form of an IPN or SIPN.

The shape may be, for example, a thread, rod or plate. One or more tissue expanders may also be mounted onto a scaffold. In a particular embodiment for use as a surgical implant in areas of the body which are curved (e.g. for cleft palate repair), the device may be in the form of a "necklace", which comprises two or more distinct tissue expanders (as subunits), which are situated and spaced apart on the scaffold. The scaffold may be fashioned from surgical-grade silver wire or barium sulfate thread. The "necklace" embodiment further allows the surgeon to tailor the length of the device for a specific surgical site by simply removing the requisite number of "redundant" subunits until the "necklace" is of the desired length.

The tissue expander of the present invention may additionally comprise an attachment site for attaching the expander to another component or part of the body. The means of attachment may be screws, bolts, adhesives or sutures.

The tissue expander of the present invention is suitable for use in the treatment of physical abnormalities or for use in making cosmetic improvements to the human or animal body. The present invention also provides a method of treating physical abnormalities or for making cosmetic improvements to the human or animal body comprising the steps of (i) surgically implanting the tissue expander as claimed in any preceding claim, (ii) allowing expansion of the tissue expander and the subsequent generation of new tissue, and, optionally, (iii) surgically removing the tissue expander. The use/method is preferably directed to humans, but may also be used for companion and show animals, e.g. cats and dogs, as well as sporting animals, e.g. horses. The cosmetic or reconstructive treatment may be in respect of congenital anomalies or acquired tissue defects.

Congenital anomalies include craniofacial or palatal clefts, syndactyly (congenitally fused fingers or toes) and giant congenital naevi. Acquired tissue defects including burns and other traumatic injuries to the skin (including leg ulcers) and soft tissue defects resulting from the surgical resection of a benign, malignant or other lesions (e.g. in post-mastectomy breast reconstruction). Anatomical regions where this technique would be particularly advantageous include the ears, nose, eyelids, lips, scalp (e.g. burn scar alopecia of the scalp), hands and feet.

The tissue expander can also be used in benign or malignant strictures of the bowel, ureter, bile duct or any other anatomical lumen including the vascular and lymphatic systems (e.g. for arterial occlusion due to atheromatous disease). Here, the tissue expander is manipulated into a substantially central hollow core in order to allow the passage of the luminal contents and thus prevent obstruction whilst the expansion process occurs. Once inserted, the tissue expander gradually expands and returns the lumen of the viscus or vessel to the desired aperture, thus alleviating the physical obstruction.

Furthermore the tissue expander can be used for internal distraction osteogenesis. That is lengthening of bone, such as the mandible. The bone is cut by the surgeon ("osteotomised"), the tissue expander is applied, and the bone slowly distracted (i.e. stretched/lengthened) over a period of time until it is of the correct proportion (at which point the expander is removed and the bone allowed to heal, although rigid internal or external fixation may be required).

Tissue expansion, and particularly anisotropic tissue expansion, has particular application in the dental field. Tooth loss is one of the most common dental problems and usually causes alveolar bone resorption. As a result, tooth replacement using a dental implant or dental prosthesis is desirable both functionally and cosmetically. For the dental implant or prosthesis to be stable it requires good bone quality and quantity which in turn may require bone grafting (or bone substitute implantation) prior to implant surgery. However, the success of the bone grafting (or bone substitute implantation e.g. hydroxyapatite) procedures in part depends on the viability and the amount of soft tissue mucosa that covers the grafted material and hence the tissue expander of the present invention may be used to facilitate these procedures by generating an adequate soft tissue envelope for this grafted material. Due to the resorption pattern of the alveolar bone which frequently has more bone loss in one particular dimension, anisotropic tissue expansion is preferred.

Another common problem in dentistry is periodontal and gingival disease. These commonly cause the loss of dental papillae, i.e. the soft tissue between the teeth. This situation is commonly termed "black triangle", and is considered cosmetically unattractive. It can be challenging for the dentist to restore this triangle. One of the current treatments is to attempt to eradicate the gap with tooth-coloured filling materials, but the results are often aesthetically suboptimal. Tissue expansion of the gingival papillae can result in lengthening of the dental papilla. This can subsequently be used to obliterate the gap with or without the use of bone graft or bone substitutes. In this instance the gingival tissue needs to be expanded anisotropically.

Further details relating to tissue expansion in the dental field may be found in A.R.M. Wittkampf, Short term experience with the subperiostel tissue expander in reconstruction of the mandibular alveolar ridge, Journal of Oral and Maxillofacial Surgery 1989, 47, 469-474; D. Lew et al, An open procedure for placement of tissue expander over the atrophic alveolar ridge, Journal of Oral and Maxillofacial Surgery 1988, 46, 161-166; D. Lew et al, The use of a subperiosteal tissue expander in rib reconstruction of an atrophic mandible, Journal of Oral and Maxillofacial Surgery 1988, 48, 229-232; and D. Lew et al, Use of subperiosteal implants with distal implants with distal fillings ports in the correction of the atrophic alveolar ridge, International Journal of Oral and Maxillofacial Surgery 1991, 20, 15-17.

The present invention will now be described with reference to the following examples which are not intended to be limiting.

EXAMPLES

Example 1

Poly(VP-co-MMA) and PLGA IPN Hydrogel

Poly(lactic-co-glycolic acid) (PLGA), 2 mmol, having a weight average molecular weight of 1,500 g/mol and acid end-groups is dissolved in 300 mL of anhydrous benzene in a 500 mL round-bottom flask under an inert nitrogen atmosphere together with 5 mmol of triethylamine. 5 mmol of acryloyl chloride is added dropwise into the PLGA solution and the mixture is stirred at 80° C. for 3 h followed by stirring at room temperature for 2 h. The reacted mixture is filtered to remove triethylamine hydrochloride and the filtrate is poured into n-hexane to precipitate and purify the macromer. The macromer precipitate is subsequently dried at room temperature under vacuum for 24 h.

Separately, a poly(VP-co-MMA) (90:10 or 99:1 PVP: PMMA) gel is fully swollen in distilled water. The gel is obtained from Polymeric Sciences Ltd (New Ash Green, Longfield, Kent, UK) and consists of pharmaceutical grade (ISO 13488) poly(methyl methacrylate) and poly(vinylpyrrolidone) with a cross-linkage density of 0.2%; alkyl methacrylate (0.2 wt %) is used as the cross-linking agent and azobisisobutyronitrile (AIBN) (0.2 wt %) as the initiator in an addition polymerisation reaction. The distilled water is periodically changed to remove the unreacted monomers or polymers not participating in the network. The fully swollen VP/MMA hydrogel is freeze-dried for 48 h. The dried VP/MMA gel is placed into the synthesised acrylate end-capped PLGA macromer solution in dichloromethane in a 40 mL vial with 0.02 wt % of cross-linker N,N'-methylenebisacrylamide (BIS) for 12 h. 0.2 wt % of initiator AIBN is added to the PLGA macromer solution to initiate the polymerisation of the macromer and cross-linker to form the PLGA network. The mixture is held at 65° C. for 3 h to form the poly(VP-co-MMA) and PLGA IPN hydrogel. The IPN gel is then purified with the excess of dichloromethane overnight and dried under vacuum at 50° C. for 24 h to form an isotropic tissue expander.

Example 2

An anisotropic tissue expander is achieved by annealing discs of the IPN obtained from Example 1 under pressure using a hand-operated hydraulic press (Specac Ltd, Orpington, Kent, UK) modified so as to contain a thermostatically controlled heating elements. The IPN is placed between plates preheated to approximately 161° C. (±3° C.) for 60 minutes and then compressed with approximately 0.0003 s$^{-1}$ of compression rate under approximately 300 MPa for a further 60 minutes. The heating cycle is then terminated and the IPN is allowed to cool to room temperature whilst being maintained under compression at the same load throughout. The cooling takes approximately 4 h. The ratio of the thickness of the uncompressed hydrogel to the compressed IPN (the compression ratio) is controlled by means of a brass mould of a pre-defined thickness. After compression, the disc type of IPN with 10 mm in diameter and 2 mm in thickness is obtained and its mass is approximately 0.2 g. The compressed IPN is stored in a sealed container purged with nitrogen until use.

Example 3

Poly(VP-co-MMA) and Polyketal IPN Hydrogel 7.2 mmol of 1,4-benzenedimethanol and 7.2 mmol of pendant unsaturated diol* with an ester group dissolved in 20 mL of ethyl acetate is added to 30 mL of benzene in a 100 mL round-bottom flask with a short path distilling head at 100° C. 0.06 mmol of recrystallised p-toluenesulfonic acid dissolved in 1.1 mL of ethyl acetate is then added. After the ethyl acetate is distilled off, 14.4 mmol of distilled 2,2-dimethoxypropane is added to initiate the reaction. 3.6 mmol of 2,2-dimethoxypropane dissolved in 2 mL of benzene is added over 30 mins 10 times with a 30 mins interval period. After about 7 hours at 100° C., the reaction is stopped by adding 200 µL of triethylamine and the mixture poured into n-hexane at 0° C. to precipitate the polyketal macromer. The macromer is filtered and washed with ether and hexane. Then the washed macromer is dried under vacuum for 24 h.

* The diol is:

Separately, the VP/MMA gel used in Example 1 is fully swollen in distilled water. The distilled water is periodically changed to remove unreacted monomers or polymers not participating in the network. The fully swollen VP/MMA hydrogel is freeze-dried for 48 h. The dried VP/MMA gel is put into the synthesised acrylate end-capped polyketal macromer solution in benzene in a 40 mL vial with 0.02 wt % of cross-linker BIS for 12 h. 0.2 wt % of initiator AIBN is added in the macromer solution to initiate the polymerisation of the macromer and cross-linker to form the polyketal network. The mixture is held at 65° C. for 6-12 h to form the poly(VP-co-MMA) and PLGA IPN hydrogel. The IPN gel is then purified with the excess of dichloromethane overnight and dried under vacuum at 50° C. for 24 h.

Example 4

An anisotropic tissue expander is achieved by compressing the IPN prepared in Example 3 as set out in Example 2.

Example 5

Poly(VP-co-MMA) and PLGA IPN Gel

A disc-shaped VP/MMA gel was placed into the synthesised acrylate end-capped PLGA macromer solution in DCM in a vial with 0.02 mmol of cross-linker BIS. Three different solution concentrations (0.025, 0.05, and 0.1 g/mL) were used. The vials containing the various solutions with the gel and crosslinkers were shaken at 50 rpm in a 37° C. water bath for 3 days to induce penetration of monomer molecules and crosslinker molecules until the gel reached to swollen state. 0.04 mmol of initiator AIBN was then added to the PLGA macromer solution to initiate the polymerization of the macromer and cross-linker to form the PLGA network which was to become the secondary network in the IPN gel. The mixture was reacted at 37° C. for 3 days and 40° C. for 2 days to form the poly(VP-co-MMA) and PLGA IPN gel. These IPN gels were then purified with excess DCM overnight and dried under vacuum at 50° C. for 48 h to remove the residual solvent. This procedure is shown schematically in FIG. 3.

Example 6

Layered Structure

Unmodified (isotropic) poly(VP-co-MMA) hydrogel is obtained from Polymeric Sciences Ltd (New Ash Green, Longfield, Kent, UK) as set out in Example 1. Rods of approximately 14 mm diameter and approximately 30 cm in length are machined/lathed to 5.77 mm. The rods are cut into multiple cylinders each approximately 6 mm in height. The cylinders are then ground down to a precise height of 6±0.1 mm and diameter of 5.77±0.1 mm.

Anisotropy is achieved by annealing the isotropic cylinders under pressure using a manual hydraulic press (Specac Ltd, Orpington, Kent, UK) fitted with thermostatically controlled heating plates. The xerogels are heated to the glass transition temperature (161±3° C. for the 90:10 co-polymer and 165±3° C. for the 99:1 co-polymer. The cylinders are gradually compressed over 1 h (at a rate of approximately 0.067 mm every minute) to a final height of 2.0 mm (giving a final compression ratio of 3:1). The cylinders are compressed at 300 MPa, 161° C. for 60 minutes (for the 90:10 co-polymer; or 165° C. for the 99:1 co-polymer). The hydrogel cylinders are cooled down to 37° C. maintaining a compression load of 300 MPa. It takes approximately 4 h for the hydrogel to cool down to room temperature. After compression the hydrogel cylinder is now approximately 2 mm in height and 10 mm in diameter. Each anisotropic cylinder is stored in a sealed container purged with nitrogen gas.

A silicone elastomer is synthesised by mixing the base agent with the catalyst or curing agent. The xerogel disc is dip-coated into the silicone solution. Subsequently the disc is mechanically rotated to allow uniform coating of the hydrogel with silicone. This produces a thin even film coating. The dip-coated hydrogel is then allowed to set in a degassed vacuum container. The dip-coating process can be repeated several times if a thicker silicone coating is required.

The biodegradable layer is produced by dip-coating the biodegradable material onto the silicone envelope that contains anisotropic hydrogel. Poly(lactic-co-glycolic acid) (PLGA) is used as the biodegradable coating and is dissolved in dichloromethane. The silicone-coated hydrogel is then dipped in the 5 wt % PLGA solution and the resulting disc is spun for 10 minutes at approximately 100-500 rpm and allowed to dry at room temperature under $N_2$ (nitrogen gas) environment for approximately 12 hours.

Example 7

Layered Structure

A silicone envelope containing an anisotropic hydrogel is obtained as set out in Example 6. The biodegradable layer is produced by spray-coating the biodegradable material onto the silicone-coated hydrogel. PLGA is dissolved in dichloromethane to create a 5 wt % solution which is used to spray-coat the device in a fume cupboard. It is allowed to dry at room temperature under $N_2$ (nitrogen gas) environment for approximately 12 hours.

Example 8

Swelling Behaviour

VP/MMA based SIPN gels with biodegradable polymer and IPN gels with biodegradable polymeric gel were prepared in a cylindrical shape. Table 1 shows the name, type and the weight % of PLGA in VP/MMA based (S-)IPN gels and the PLGA concentration used for the preparation of the gels.

TABLE 1

The name and type of the (S-)IPN gels, PLGA content and the PLGA concentration used

| Gel Name | Gel Type | PLGA Content (wt %) | PLGA Concentration (g/mL) |
|---|---|---|---|
| VM | normal | 0 | — |
| VMLG-s1 | semi-IPN | 9.0 | 0.025 |
| VMLG-s2 | semi-IPN | 13 | 0.050 |
| VMLG-s3 | semi-IPN | 20 | 0.100 |
| VMLG-s4 | semi-IPN | 28 | 0.200 |
| VMLG-I1 | IPN | 45 | 0.025 |
| VMLG-I2 | IPN | 60 | 0.050 |
| VMLG-I3 | IPN | 70 | 0.100 |
| LG | normal | 100 | 0.100 |

The PLGA content for each gel was obtained from equation (1).

$$m^{LG}\% = \frac{m_i - m^{VM}}{m_i} \times 100\% \tag{1}$$

where the $m^{LG}\%$ is the mass percentage of PLGA in each hydrogel and the $m^{VM}$ is the mass of VP/MMA dry gel before including PLGA.

The untreated VP/MMA (VM) gel was used as the control against which to compare the swelling behaviour of all the hydrogel systems prepared for this example. The VMLG-s gel series are semi-IPN gels comprising VP/MMA network and PLGA polymers. The VMLG-l gel series are IPN gels composing of VP/MMA network and PLGA network. LG gel contains only PLGA. The PLGA content in the gels has increased with increasing the PLGA concentration used for the preparation of (S-)IPN gels. As shown in Table 1, although the same PLGA concentration and the same time and temperature for the diffusion of PLGA chain into a VP/MMA gel were used for preparing both SIPN gel and IPN gels, the PLGA content in the gels is seen to be higher in the IPN gels. VMLG-s2 gel has 13 wt % of PLGA and VMLG-12 gel has 60 wt % when 0.05 g/mL of PLGA solution was used. This is likely to have arisen because a relatively lower molecular weight PLGA was used for IPN gels compared to the SIPN gels, resulting in higher amounts of PLGA molecules diffusing into the primary network (VM gel). The in-diffused PLGA molecules formed a secondary network as the IPN and so could not then diffuse out. On the other hand, during the preparation of SIPN gel the diffusion of PLGA molecules into and out of the VM primary network was counterbalanced to some extent.

The swelling behaviour of the various (S-)IPN gels was investigated and compared with VP/MMA gels by monitoring the mass swelling ratio (q) as a function of time. In this work, after drying of the various (S-)IPN gels with different PLGA contents in vacuum at 60° C. for at least 48 hours, they were immersed into Hartmann's solution at pH 7.4 at 37° C. The hydrogels were taken out from the solution at periodic intervals of time and their masses at the time ($m_T$) were measured after gently removing surface water with filter paper. Then, the swollen hydrogel fully dried in vacuum at 60° C. for at least 48 hours, from which the mass of the dried hydrogel ($m_d$) was also measured. By this procedure, the mass swelling ratio (q) was determined by using equation (2).

$$q = \frac{m_T}{m_d} \tag{2}$$

Figure 6:
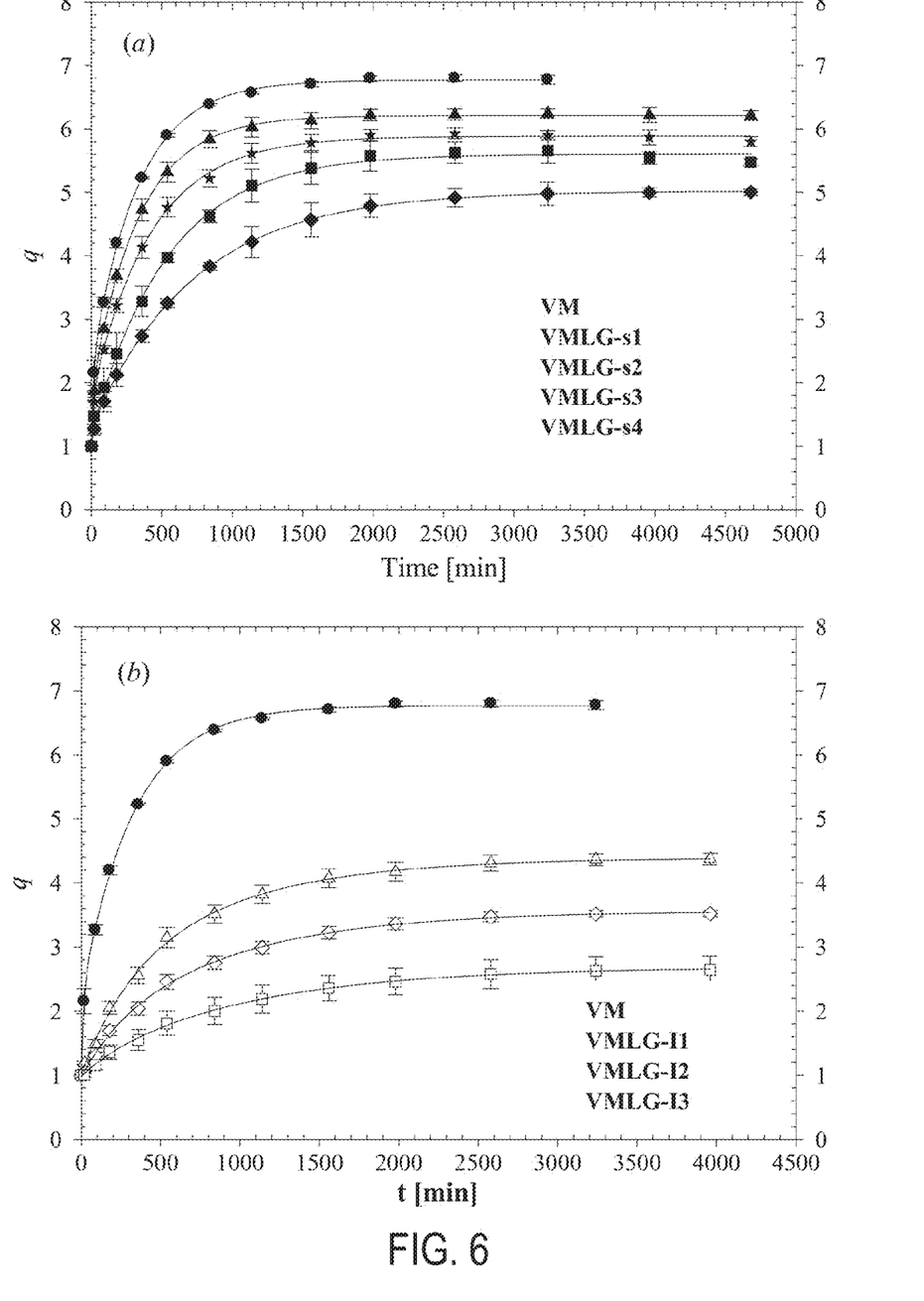
FIG. 6 shows the swelling ratio q as a function of time for (a) SIPN gels and (b) IPN gels synthesised with different PLGA contents in Hartmann's solution at 37° C. and (c) photographs of the VM, VMLG-s2, and VMLG-l2 hydrogels taken at 0, 90, 540 and 3,240 min.
Figure 6C:
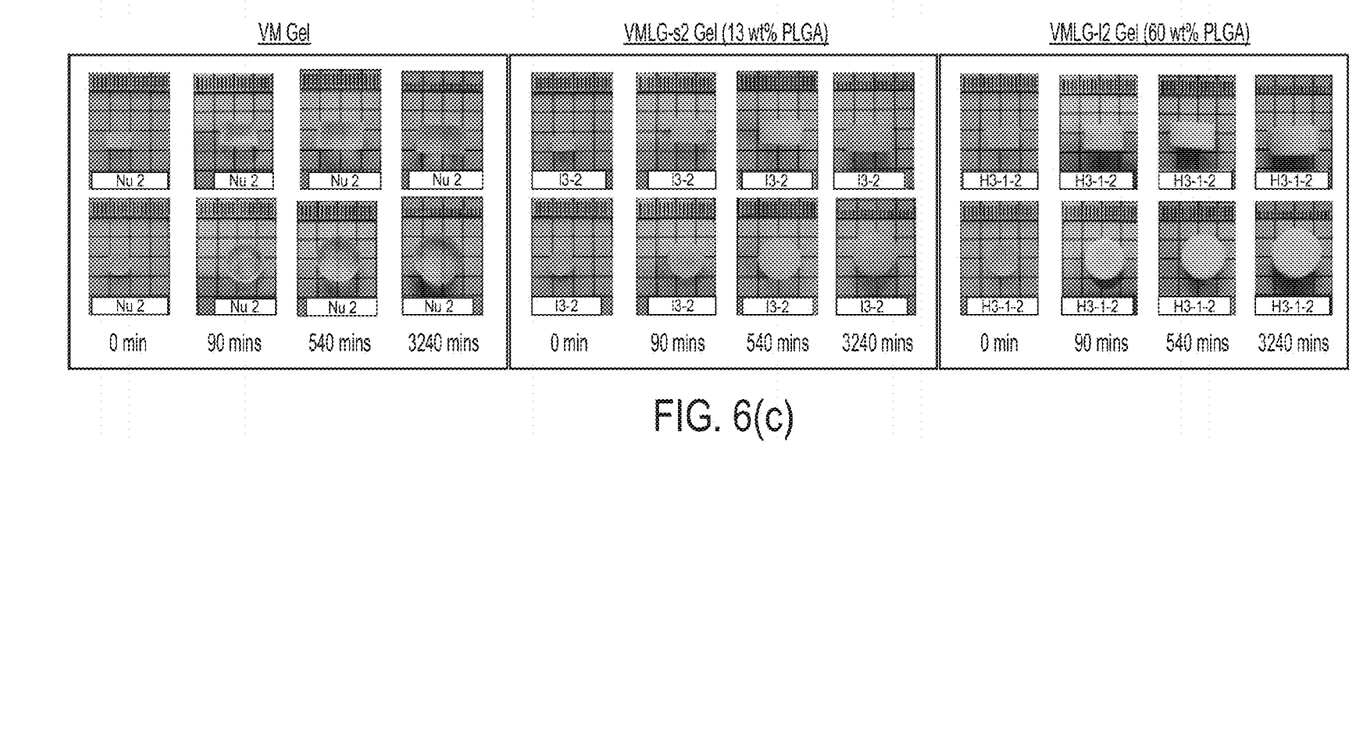

FIGS. 6(a) and (b) show how the swelling ratio q of the SIPN hydrogels and IPN hydrogels, respectively, changes as a function of swelling time for different PLGA contents. The q of all hydrogels initially increases fast and then the increase is getting to slow down finally. Overall, the untreated VM gels showed the fastest swelling rates, followed by the SIPN (VMLG-s) gels and finally the IPN (VMLG-l) gels. With increasing PLGA content in SIPN and IPN gels, their swelling rates were observed to decrease. This is considered to be because the more content of PLGA interpenetrating into the VM gel, which all VP/MMA and PLGA SIPN and IPN gel use as the primary network, produced not only the smaller network mesh size, which may be caused by additional crosslinks or entanglements, but also more hydrophobic properties. Consequently, the diffusion of water molecules into the gels with higher PLGA content more restricted, resulting in the slower swelling of gels.

FIG. 6(c) shows the photographs of dry and swollen states of VM, VMLG-s2, and VMLG-l2 gels taken at 0, 90, 540 and 3,240 min. The upper row of photographs shows the side view of the gels or hydrogels and the lower row shows the front view. It is noticeable that the size of the hydrogels increased with time, which agrees with increasing value of q as a function of time. Besides, while the VM hydrogels are transparent, the VMLG-s2 hydrogels are milky and VMLG-l2 hydrogels are whiter than VMLG-s2 hydrogels. This white colour is presumably due to the PLGA. In general, the IPN gels were found to include more of the PLGA than the SIPN gels. This is because the low molecular weight PLGA macromers readily diffused into the primary gel, and once cross-linked to form the secondary network thus could not diffuse out. On the other hand, for the SIPN hydrogels some outward diffusion could have occurred during processing. Thus the IPN gels will have a greater relative content of the hydrophobic PLGA and hence show slower swelling rate.

It is also shown that while VM hydrogels show the saturated swelling ratio, with increasing PLGA content SIPN and IPN hydrogels do not show saturated value in swelling ratio. This means that the hydrogels kept swelling. It is expected that the hydrogels will continue to swell until all of the PLGA degrades and diffuses out from the hydrogels, so finally only non-degradable component will remain. With increasing PLGA content, the time to reach the saturation point in swelling ratio will take longer. Conclusively, it is thought that the value of swelling ratio as well as swelling rate are dependent on the composition of gels. Thus by modulating the composition of biodegradable component and primary gel, the swelling behaviour can be controlled.

This example shows that it is possible to design a hydrogel system with an expected and controlled time dependent swelling behaviour by the semi-IPN and IPN hydrogels prepared by adding a biocompatible and biodegradable polymer such as PLGA in a non-degradable and covalently-connected network hydrogels.

The invention claimed is:

1. A tissue expander comprising a self-inflating polymer network and a biodegradable polymer having a non-degraded state and a degraded state, wherein the biodegradable polymer constrains the inflation of the self-inflating polymer network in the non-degraded state by restricting the inflation of the self-inflating polymer network by physical means, and the biodegradable polymer allows inflation of the self-inflating polymer network in the degraded state;

wherein the self-inflating polymer network and the biodegradable polymer form an interpenetrating or semi-interpenetrating polymer network wherein the self-inflating polymer network forms the primary network and the biodegradable polymer forms the secondary network, or wherein the self-inflating polymer network forms a core and the biodegradable polymer forms a coating which surrounds the core, and where the biodegradable polymer has a modulus of 0.01-10 GPa in the xerogel state as measured in the absence of the self-inflating polymer.

2. A tissue expander as claimed in claim 1, wherein the self-inflating polymer network has a compression ratio of 2:1-20:1.

3. A tissue expander as claimed in claim 1, wherein the self-inflating polymer network generates a swelling pressure of 1-50 kPa/cm$^2$.

4. A tissue expander as claimed in claim 1, wherein the self-inflating polymer network is a xerogel/hydrogel.

5. A tissue expander as claimed in claim 1, wherein the self-inflating polymer network comprises at least two different monomers.

6. A tissue expander as claimed in claim 1, wherein the self-inflating polymer network comprises at least one monomer containing —COOH, >C=O, —OH, or —NH$_2$ groups.

7. A tissue expander as claimed in claim 1, wherein the biodegradable polymer degrades from the non-degraded state to the degraded state over a period of at least 2 days.

8. A tissue expander as claimed in claim 1, wherein the biodegradable polymer is based on a polymer selected from polymers or co-polymers of glycolic acid and/or lactic acid, poly(dioxanone) (PDO), poly(trimethylene carbonate) (PTMC), poly(ε-caprolactone) (PCL), polyanhydrides, polyhydroxybutyrate (PHV), polyorthoesters, polyketals, polyacetals, polyphosphazenes, polyhydroxybutyrate (PHB), polyhydroxyvalerate (PHV), polycyanoacrylates, poly(amino acids), poly(propylene fumarate), fibrin, collagen, gelatin, hyaluronan, chondrin, starch, glycogen, cellulose and chitosan, as well as polymer blends and co-polymers of two or more of these polymers.

9. A tissue expander as claimed in claim 1, wherein the self-inflating polymer network and the biodegradable polymer form an interpenetrating polymer network.

10. A tissue expander as claimed in claim 1, wherein the self-inflating polymer network and the biodegradable polymer form a semi-interpenetrating polymer network.

11. A tissue expander as claimed in claim 1, wherein the self-inflating polymer network forms a core and the biodegradable polymer forms a coating which surrounds the core.

12. A tissue expander as claimed in claim 1, further comprising a coating layer, which coating layer optionally further comprising water-soluble filter particles.

13. A tissue expander as claimed in claim 1, which further incorporates a pharmaceutically active ingredient and/or a radio-opacifier.

14. A method of treating physical abnormalities or for making cosmetic improvements to the human or animal body comprising the steps of (1) surgically implanting the tissue expander as claimed in claim 1, (ii) allowing expansion of the tissue expander and the subsequent generation of new tissue, and, optionally, (iii) surgically removing the tissue expander.

* * * * *